United States Patent
Tanaka et al.

(10) Patent No.: US 9,909,090 B2
(45) Date of Patent: Mar. 6, 2018

(54) CELL CULTURE KIT, AND METHOD OF USING CELL CULTURE KIT

(71) Applicant: Toyo Seikan Group Holdings, Ltd., Tokyo (JP)

(72) Inventors: Satoshi Tanaka, Kanagawa (JP); Takahiko Totani, Kanagawa (JP); Yoichi Ishizaki, Kanagawa (JP)

(73) Assignee: TOYO SEIKAN GROUP HOLDINGS, LTD, Tokyo (JP)

( * ) Notice: Subject to any disclaimer, the term of this patent is extended or adjusted under 35 U.S.C. 154(b) by 93 days.

(21) Appl. No.: 14/444,479

(22) Filed: Jul. 28, 2014

(65) Prior Publication Data

US 2014/0335608 A1    Nov. 13, 2014

Related U.S. Application Data

(63) Continuation of application No. PCT/JP2013/000410, filed on Jan. 28, 2013.

(30) Foreign Application Priority Data

Feb. 1, 2012    (JP) ................................. 2012-019559

(51) Int. Cl.
*C12M 1/00*    (2006.01)
*C12M 1/04*    (2006.01)
*C12M 3/00*    (2006.01)

(52) U.S. Cl.
CPC ............ *C12M 23/34* (2013.01); *C12M 23/14* (2013.01); *C12M 23/24* (2013.01); *C12M 23/26* (2013.01); *C12M 29/26* (2013.01)

(58) Field of Classification Search
CPC ...... C12M 23/34; C12M 23/14; C12M 23/24; C12M 23/26; C12M 29/26; C12M 33/00; C12M 33/04; C12M 33/07
(Continued)

(56) References Cited

U.S. PATENT DOCUMENTS 4,073,691 A * 2/1978 Ahnell ..................... C12Q 1/04
435/287.1
4,360,435 A * 11/1982 Bellamy ................. A61L 2/022
210/636
(Continued)

FOREIGN PATENT DOCUMENTS

CN    101370928 A    2/2009
JP    63503201 A    11/1988
(Continued)

OTHER PUBLICATIONS

Extended European Search Report issued in corresponding European Application No. 13743029.4 dated Aug. 19, 2015 (5 pages).
(Continued)

*Primary Examiner* — Nathan A Bowers
(74) *Attorney, Agent, or Firm* — Osha Liang LLP

(57) ABSTRACT

A cell culture kit for cultivating cells in a closed system includes at least one or more of each of: a culture container for cultivating cells; a culture medium storage container for storing a culture medium or the like; a cell injection container for injecting cells; and a cell collecting container for collecting a suspension of cells after cultivation; wherein the culture medium storage container is also used as a waste liquid container for collecting a culture medium after cultivation, and the culture container, the culture medium storage container, the cell injection container and the cell collecting container are linked to one another through a conduit.

15 Claims, 6 Drawing Sheets

(58) Field of Classification Search
USPC .................................................. 435/289.1
See application file for complete search history.

(56) References Cited

U.S. PATENT DOCUMENTS

| | | | | |
|---|---|---|---|---|
| 4,829,002 | A | * | 5/1989 | Pattillo .................. C12M 33/07 141/244 |
| 2010/0062530 | A1 | * | 3/2010 | Tanaka .................. C12M 41/26 435/383 |
| 2010/0317102 | A1 | | 12/2010 | Suzuki et al. |
| 2013/0157353 | A1 | | 6/2013 | Dijkhuizen Borgart et al. |
| 2013/0344597 | A1 | | 12/2013 | Suzuki et al. |

FOREIGN PATENT DOCUMENTS

| | | |
|---|---|---|
| JP | 2004008111 A | 1/2004 |
| JP | 2004073084 A | 3/2004 |
| JP | 2005-287425 A | 10/2005 |
| JP | 2006/262876 A | 10/2006 |
| JP | 2007175028 A | 7/2007 |
| JP | 2007295827 A | 11/2007 |
| JP | 2008048644 A | 3/2008 |
| JP | 2008-271850 A | 11/2008 |
| WO | 2007052716 A1 | 5/2007 |
| WO | 2011/142670 A1 | 11/2011 |

OTHER PUBLICATIONS

Office Action issued in corresponding Chinese Application No. 201380007337.9 dated Apr. 3, 2015, and English translation thereof (11 pages).
International Search Report issued in PCT/JP2013/000410 dated Mar. 12, 2013 (2 pages).
International Preliminary Report on Patentability and Written Opinion issued in PCT/JP2013/000410 dated Aug. 14, 2014 (8 pages).
Notification of Reasons for Refusal (Office Action) dated Mar. 28, 2017, issued by the Japan Patent Office in corresponding Japanese Patent Application No. JP 2013-556254, with English translation (9 pages).

* cited by examiner

US 9,909,090 B2

CELL CULTURE KIT, AND METHOD OF USING CELL CULTURE KIT

CROSS-REFERENCE TO RELATED APPLICATIONS

This application claims the benefit of International Patent Application No. PCT/JP2013/000410, filed on Jan. 28, 2013, which is incorporated by reference in its entirety.

TECHNICAL FIELD

The present invention relates to a kit for cell culture (hereinafter abbreviated as "cell culture kit") for use in an automatic cell culture device whereby cell cultivation is conducted by using a culture container and a method for using the same.

BACKGROUND ART

In recent years, in the fields of production of medicines, gene therapy, regenerative medicine, immunotherapy or the like, there has been a demand for cultivating a large amount of cells, tissues, microorganisms or the like efficiently in an artificial environment.

In such cultivation of a large amount of cells, an automatic cell culture device wherein cell culture is automatically conducted by using a culture container can preferably be used.

When using an automatic cell culture device, it is important to use it in a closed system in order to suppress the risk of contamination. However, a cell culture kit that enables automatic culture that includes a process from injection of cells, addition of a culture medium, sampling to collection while keeping a closed system was not available so far.

RELATED ART DOCUMENT

Patent Document

Patent Document 1: WO2007/052716

SUMMARY OF THE INVENTION

Problems to be Solved by the Invention

That is, up to date, several automatic cell culture devices were proposed, and also a container kit for use in this device was proposed. However, a cell culture kit that can execute easily a process from injection of cells, addition of a culture medium, sampling to collection, that is required when used in clinical stages, while keeping a closed system in the kit was not present.

Specifically, as the automatic cell culture device for conducting automatic cell culture using a culture container, the cell culture device disclosed in Patent Document 1 can be given, for example. In this device, a culture medium storage means, a culture container for developing functions and a culture container for proliferation are configured as a closed system. However, in this cell culture device, for exchanging a waste liquid bag for a cell collection bag, no configuration capable of keeping a closed system is provided and it is considered that, in this device, exchange of a waste liquid bag for a cell collection bag is conducted in an open system. Other than the device, no cell culture kit has been found that enables a process from injection of cells to collection of cells to be realized while keeping a closed system in the kit.

Further, when using an automatic cell culture device, a culture medium storage container in a cell culture kit is often refrigerated. However, if a culture medium that is refrigerated is directly supplied from a cell culture storage container to a culture container, a problem occurs that the temperature of a culture medium in a culture container is lowered, and as a result, proliferation of cells is deteriorated.

In addition, a refrigerated culture medium has a high solubility for a gas, and hence, a large amount of carbon gas or oxygen is dissolved therein. If such a medium is transferred to a culture container and heated, a problem arises that air bubbles are generated in a culture container since the solubility for a gas is lowered with an increase in liquid temperature. Air bubbles generated in a culture container are finely foamed when stirring the inside of the container, thereby adversely affecting cells. Further, there is also a problem that, due to air bubbles, the inside of a container cannot be seen clearly, resulting in difficulty in observation.

In order to solve these problems, one of conceivable measures is to heat a culture medium storage container itself. However, if a culture medium is heated for a long period of time, proliferation efficiency of cells is lowered. Therefore, if possible, it is desirable to refrigerate a culture medium until immediately before cultivation.

The present invention has been made in view of the above-mentioned circumstances, and one object thereof is to provide a cell culture kit that enables, in cell culture using a cell culture container, a process from cell injection, addition of a culture medium, sampling to collection to be conducted automatically in a kit while keeping a closed system.

Another object of the present invention to provide a cell culture kit having a temperature control container for adjusting the temperature of the medium and a method for using the same.

Means for Solving the Problems

In order attain the above-mentioned object, the cell culture kit of the present invention is a cell culture kit for cultivating cells in a closed system that comprises at least one or more of each of:

a culture container for cultivating cells;
a culture medium storage container for storing a culture medium or the like;
a cell injection container for injecting cells and
a cell collecting container for collecting a suspension of cells after cultivation, wherein the culture medium storage container is also used as a waste liquid container for collecting a culture medium after cultivation, and the culture container, the culture medium storage container, the cell injection container and the cell collecting container are linked to one another through a conduit.

Further, it is preferred that the cell culture kit of the present invention have a configuration in which it is provided with at least one or more sampling containers capable of sampling part of a culture medium during cultivation and the sampling container is linked to a conduit.

Further, it is preferred that the cell culture kit of the present invention have a configuration in which a temperature control container for controlling the temperature of a culture medium or the like is branched from a conduit linking the culture container and the culture medium storage container and also preferred that part or all of a culture medium or the like that refrigerated in the culture medium storage container be transferred to the temperature control container, heated to a predetermined temperature and then transferred to the container.

The method for using a cell culture kit of the present invention is a method characterized in that, the cell culture kit is provided with at least one or more of:

a culture container for cultivating cells; a culture medium storage container for storing a culture medium or the like; a cell injection container for injecting cells; a cell collecting container for collecting a suspension of cells after cultivation; and a temperature control container for controlling the temperature of a culture medium or the like; wherein the culture medium storage container is also used as a waste liquid container for collecting a culture medium after cultivation, the culture container, the culture medium storage container, the cell injection container, the cell collecting container and the temperature control container are linked to one another through a conduit, a culture medium or the like is refrigerated in the culture medium storage container, part or all of the culture medium or the like thus refrigerated is transferred from the culture medium storage container to the temperature control container, the culture medium or the like is heated to a prescribed temperature in the temperature control container, and the culture medium or the like of which the temperature has been adjusted is transferred to the culture container.

Advantageous Effects of the Invention

In the cell culture using a culture container, a process from injection of cells, addition of a culture medium, sampling to collection can be conducted while keeping a closed system in the kit. Further, since it becomes possible that a culture medium that is refrigerated in the culture medium storage container is transferred to a temperature control container where the temperature of the culture medium is adjusted and the culture medium is then transferred to the culture container, lowering in temperature of the culture medium in the culture container can be prevented and proliferation of cells can be prevented from being hindered.

BEST MODE FOR CARRYING OUT THE INVENTION

Preferred embodiments of the cell culture kit of the present invention will be explained with reference to the drawings.

First Embodiment

Figure 1:
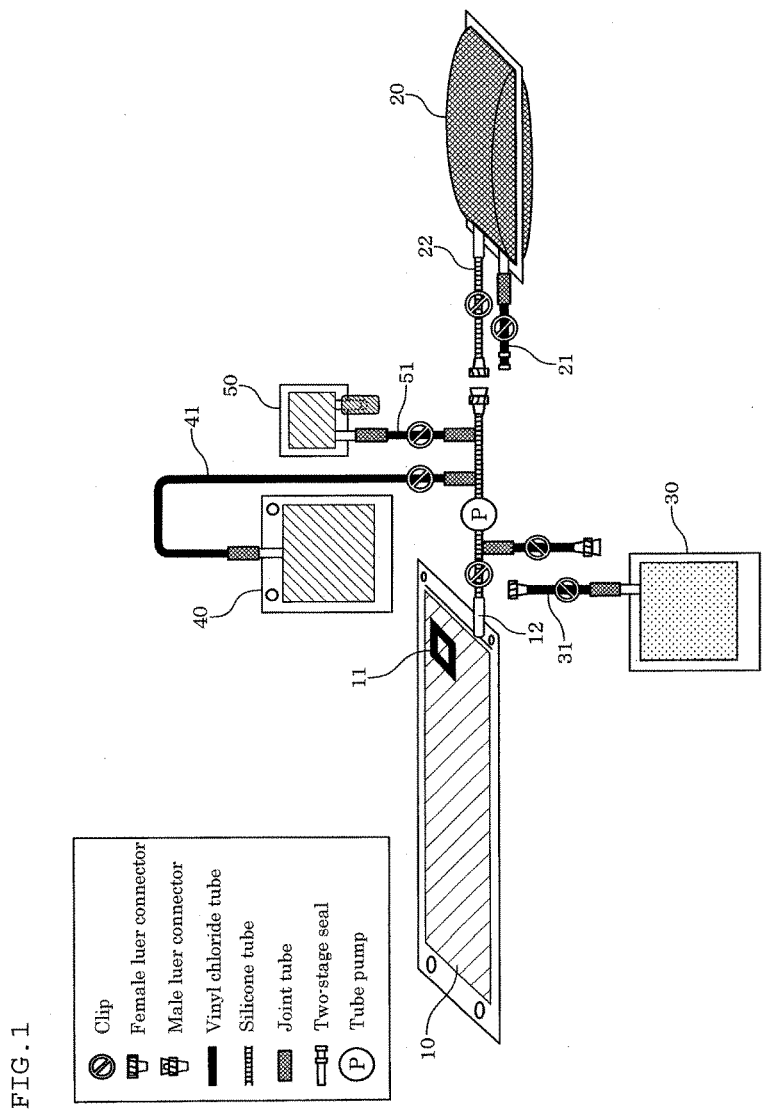
FIG. 1 is a view showing a configuration of a cell culture kit according to the first embodiment (1 port-configuration) of the present invention.

The first embodiment of the present invention will be explained with reference to FIG. 1. FIG. 1 is a view showing the configuration of the cell culture kit of this embodiment.

The cell culture kit of this embodiment is provided with a culture container 10, a culture medium storage container 20, a cell injection container 30 and a cell collecting container 40. It is preferred that the kit be provided with a sampling container 50.

The culture container is a container made of a flexible material and formed in a bag. In this container, a culture medium (culture liquid) is placed, and cells to be cultivated are disseminated therein for cultivation of a large amount of cells.

The culture container 10 is required to have gas permeability that is required for cultivation of cells. Specifically, it is preferred that the culture container 10 have an oxygen transparency of 5000 ml/m$^2$·day·atm (37° C.-80% RH) or more.

In order to allow the contents to be visible, it is preferred that all or part of the culture container 10 have transparency. In FIG. 1, an observation frame 11 is provided on the culture container 10. This frame serves to suppress generation of wrinkles and enables observation of the inside of the bag to be conducted easily.

Further, in order to achieve a high cell proliferation efficiency, it is preferred that the culture container 10 have low cytotoxicity, low elution properties and radiation resistance.

As the material of the culture container 10 that satisfies these conditions, a polyethylene-based resin is preferable. As the polyethylene-based resin, polyethylene, a copolymer of ethylene and α-olefin, a copolymer of ethylene and vinyl acetate, and an ionomer using a copolymer of ethylene and acrylic acid or methacrylic acid and a metal ion or the like can be given. Also, polyolefin, a styrene-based elastomer, a polyester-based thermoplastic elastomer, a silicone-based thermoplastic elastomer, a silicone resin or the like can also be used.

The culture container 10 is provided with a port through which injection or collection of a culture medium or cells are conducted. No restrictions are imposed on the number of this port. However, as mentioned later, a culture container having one to three ports is preferably used.

The culture medium storage container 20 is a container for accommodating a culture medium for cultivating cells to be transferred to the culture container 10. In order to prevent a great change in pH of the culture medium accommodated therein, it is preferred that the culture medium storage container 20 have gas barrier properties. Specifically, it is preferred that the culture medium storage container 20 have a carbon dioxide transmittance of 1000 ml/m$^2$·day·atm (23° C.-80% RH) or less. The reason therefor is as follows. It is desired that the amount of carbon dioxide leaking outside from the inside of the culture medium storage container 20 be suppressed as small as possible in order to eliminate escaping of a high-concentration carbon gas contained in a culture medium to the air, and to prevent lowering in carbon gas concentration in a culture medium and in an eventual increase in pH.

It is preferred that the culture medium storage container 20 have at least two ports. To one of these ports, a conduit (tube) that is linked to the culture container 10 is connected. From this culture medium storage container 20, a fresh culture medium is transferred little by little to the culture container 10 in accordance with the degree of proliferation of cultured cells or the like. It is preferred that the culture medium storage container 20 in which the culture medium is sealed be stored in a refrigerator. Another port of the culture medium storage container 20 is a culture medium filling port 21 for supplying a culture medium from the outside of the cell culture kit of this embodiment to the culture medium storage container 20. Through an aseptic conjunction device or the like, a culture medium is filled from this culture medium filling port 21.

The cell culture kit of this embodiment can be configured by using the culture medium storage container 20 provided with only one port. In this case, it is possible to transfer the culture medium from this port to the culture container 10 after filling a culture medium in the culture medium storage container 20.

Further, the culture medium storage container 20 can be used as a waste liquid container after completion of cultivation. That is, prior to collection of cells from the culture container 10 to a cell collecting container 40, a supernatant of the culture medium is transferred to the culture medium storage device 20 serving as the waste liquid container. As a result, a concentrated suspension of cells can be transferred from the culture container 10 to the cell collecting container 40. The same can be applied to the second embodiment where no dedicated waste liquid container is used.

In the cell culture kit of this embodiment, it is possible to provide two or more of the culture medium storage containers 20. Due to such a configuration, not only twice the amount of the same culture medium can be stored but also, by storing different culture mediums in different storage containers, a culture medium can be supplied to the culture container 10 in various modes.

A cell injection container 30 is a container in which cells and a culture medium that are required at the time of starting cultivation are accommodated. By transferring the contents in this container to the culture container 10, cultivation starts. It is preferred that the amount of cells and a culture medium to be put in the cell injection container 30 be about 250 ml in total. The amount is, however, not limited thereto.

Further, since the cell injection container 30 is a container for accommodating cells and a culture medium, it is preferred that it have gas permeability as in the case of the culture container 10. In addition, it is preferred that the cell injection container 30 have low cytotoxicity, low elution properties or the like. Therefore, as the material of the cell injection container 30, it is preferable to use the same material as that of the cell culture 10.

This cell injection container 30 is provided with at least one port. Cells and a culture medium at the time of starting cultivation are sent from the cell injection container 30 to the culture container 10 through this port.

The cell collecting container 40 is a container for collecting part of cultured cells and a culture medium from the culture container 10 after cultivation. Therefore, it is preferred that the cell collecting container 40 have the same properties as those of the culture container 10. As the material therefor, it is preferable to use the same material as that of the culture container 10.

The cell collecting container 40 is provided with at least one port. Part of cells and a culture medium are sent from the culture container 10 to the cell collecting container 40 through this port.

The sampling container 50 is a container for conducting sampling. Specifically, during or after cultivation of cells, part of a suspension of cells in the culture container 10 is transferred to the sampling container 50 for sampling. As the amount of a sample to be transferred to the sampling container 50, about 10 ml is preferable, for example. The amount of a sample is not limited to thereto.

The sampling container 50 is provided with two ports. One of these ports is connected to a conduit (tube) that is linked to the culture container 10, whereby a suspension of cells is sent from the culture container 10 to the sampling container 50. Another port is used for taking out part of a suspension of cells in the sampling container 50 for conducting various analyses. A configuration in which only one port is provided to conduct both sending and take-out or a configuration in which three or more ports are provided to conduct sending and take-out a plurality of times can be possible.

Next, an explanation will be made on a conduit that connects containers in the cell culture kit of this embodiment.

As the materials of these conduits, it is desirable to select an appropriate one depending on the intended use. For example, a silicone resin, soft vinyl chloride resins, polybutadiene resins, an ethylene-vinyl acetate copolymer, polyurethane-based thermoplastic elastomers, polyester-based thermoplastic elastomers, silicone-based thermoplastic elastomers, styrene-based elastomers such as SBS (styrene-butadiene-styrene), SIS (styrene-isoprene-styrene), SEBS (styrene-ethylene-butylene-styrene) and SEPS (styrene-ethylene-propylene-styrene), polyolefin resins, fluorine resins or the like can be used.

In the cell culture kit of this embodiment, as roughly divided, two different types of conduits can be used.

That is, a culture medium supplying tube for connecting the culture container 10 and the culture medium storage container 20, and a culture medium transferring tube that connects between combination of other containers.

As the culture medium supplying tube for connecting the culture container 10 and the culture medium storage container 20, it is particularly preferable to use one made of a polyolefin resin or a silicone resin. As for the culture medium supplying tube, since it is used for transferring a culture medium to the culture container 10 little by little throughout the cultivation period, it is desirable to have especially excellent low cytotoxicity, low elution properties or the like. During the process of cultivation, it is not required to fuse this culture medium supplying tube. Taking these into consideration, it is preferred that the tube be made of the above-mentioned material.

In FIG. 1, the culture medium storage container connecting tube 22 is assumed to be made of such culture medium supplying tube. For example, a silicone tube having an inner diameter of 3.5 mm and an outer diameter of 6.0 mm can be preferably used.

As for the culture medium transferring tube that connects between combinations of other containers, since it is not used to transfer a culture medium for a long period of time, a high degree of low cytotoxicity, low elution properties or the like are not required. In addition, by fusing the conduit, it is desirable to enable the cell injection container, the cell collecting container (waste liquid container) and the sampling container to be capable of being removed from the cell culture kit of this embodiment and to enable them to be used while keeping a closed system in the kit.

As the culture medium transferring tube to be connected to these containers, it is preferable to use one in which at least one portion thereof is made of a thermoplastic resin. It is also possible that the entire culture medium transferring tube be formed of a thermoplastic resin.

As the thermoplastic resin, a soft vinyl chloride resin can be used, for example. A usable resin is not restricted thereto.

In FIG. 1, it is assumed that a cell injection container connecting tube 31, a cell collecting container connecting tube 41 and a sampling container connecting tube 51 are formed of such a culture medium transferring tube. For example, a vinyl chloride tube having an inner diameter of 3.3 mm and an outer diameter of 5.0 mm can preferably be used.

To a port forming the culture medium filling port 21 for supplying a culture medium from the outside of the cell culture kit of this embodiment to the culture medium storage container 20, it is preferable to connect a tube made of a thermoplastic resin, in particular a tube formed of a soft vinyl chloride resin. The reason therefor is as follows. In the culture medium storage container 20, a culture medium is filled in this culture medium filling port 21 through an aseptic conjunction device. Currently, for connection to this aseptic conjunction device, a soft vinyl chloride resin is mainly used. For processing the tip of the tube, in addition to the two-stage seal of this embodiment, an element such as a luer connector, a needleless connector and a septum can be used.

As shown in FIG. 1, the cell culture kit of this embodiment has a one-port configuration in which only one port is provided in the culture container 10.

That is, in the cell culture kit of this embodiment, a first port 12 is provided in the culture container 10, and to this first port 12, the culture medium storage container 20 is connected through the culture medium storage container connecting tube 22. Other containers are connected to this culture medium storage container connecting tube 22.

That is, through the cell injection container connecting tube 31, the cell injection container 30 is connected to the culture medium storage container connecting tube 22. Further, through the cell collecting container connecting tube 41, the cell collecting container 40 is connected to the culture medium storage connecting tube 22. Further, through the sampling container connecting tube 51, the sampling container 50 is connected to the culture medium storage connecting tube 22. A tube pump is provided only in the culture medium storage connecting tube 22.

Here, it is preferred that the cell injection containers 30 be connected to a position closer to the culture container 10 in the culture medium storage connecting tube 22. Due to such a configuration, it is possible that, when the culture medium is injected to the culture container 10 from the culture medium storage container 20 at the time of starting cultivation, it is possible to minimize entrance of air in the culture medium storage connecting tube 22 to the culture container 10.

Specifically, at first, a culture medium is sent from the culture medium storage container 20 to the cell injection container 30, and the inside of a conduit connecting the culture medium storage container 20 and the cell injection container 30 is filled with the culture medium. At this time, the air present in the inside of the conduit is moved to the inside of the cell injection container 30. Subsequently, when cells and a culture medium are sent from the cell injection container 30 to the cell culture container 10, the air inside the cell injection container 30 is moved upward, whereby only cells and culture mediums can be sent from the cell injection container 30 to the cell culture container 10.

Therefore, only air that is present in a region from a part close to the culture medium storage container connecting tube 22 to which the cell injection container 30 is connected to the culture container 10 enters the culture container 10. As a result, in the culture medium storage container connecting tube 22, by allowing the cell injection container 30 to be connected to a position as closer as possible to the culture container 10, the amount of air sent to the culture container 10 can be minimized to a level that does not hinder observation or photographing of cells.

Further, at least as for the culture medium storage container 20 and the cell injection container 30, it is preferred that they be configured such that they can be removable in the cell culture kit. The reason therefor is that, by this configuration, prior to use, a culture medium is filled in the culture medium storage container 20 and cells and a culture medium are filled in the cell injecting container 30, and they can be used in the state being connected to the cell culture kit at the time of use. It is preferred that the culture container 10, the cell collecting container 40, the sampling container 50 and tubes attaching thereto, etc. be integrally configured before use (at the time of production). A waste liquid container 60 (mentioned later) also can be integrally configured before use.

Further, it is preferred that each tube be provided with a clip or an electromagnetic valve so that transfer of a culture medium or the like in each tube be controlled.

In a joint portion in the culture medium storage container connecting tube 22, a luer connector (needleless connector) with a cap or a cover or the like can be used.

In the cell culture kit of this embodiment, a silicone tube is used for the culture medium storage container connecting tube 22, and a vinyl chloride tube is used for other tubes. According to need, a joint tube (for example, one having an inner diameter of 5.3 mm and an outer diameter of 7.0 mm) is used. The present invention is not restricted to such specific configurations.

The cell culture kit of this embodiment can be used by the following method, for example.

First, in the cell culture kit shown in FIG. 1, a connector in the culture medium storage connecting tube 22 of the culture medium storage container 20 filled with a culture medium is connected, and the cell injection container connecting tube 31 of the cell injection container 30 is connected by means of a connector.

Then, from the culture medium storage container 20, through the culture medium storage container connecting tube 22 and the cell injection connecting tube 31, a culture medium is transferred to the cell injection container 30. At this time, air in the part of the tube in which a culture medium has been transferred enters the cell injection container 30.

Subsequently, cells and a culture medium are transferred from the cell injection container 30 to the culture container 10. At this time, by arranging the cell injection container 30 upright with the port directing downward to collect the air in the cell injection container 30 in the top portion, only cells and a culture medium can be transferred to the culture container 10 without sending air to the culture container 10.

Subsequently, from the culture medium storage container 20, a culture medium is transferred to the culture container 10 through the culture medium container connecting tube 22. The timing at which cells and a culture medium are transferred from the cell injection container 30 to the culture container 10 is not limited to that mentioned above. For example, transfer can be conducted after part or all of the culture medium is transferred from the culture medium storage container 20 to the culture container 10.

After a prescribed amount of a culture medium and cells are filled in the culture container 10, shaking or stirring is conducted appropriately, and then, cultivation of cells is conducted for a prescribed period of time. During cultivation of cells, by appropriately transferring a sample from the culture container 10 to the sampling container 50, the sample can be used for examination or analysis.

After completion of cell culture for a prescribed period of time, cells are collected. At this time, the culture medium storage container 20 is used as a waste liquid container.

That is, at first, the culture container 10 is brought into a state of rest to allow cells to settle in the lower part. Thereafter, a supernatant of a suspension of cells is transferred from the culture container 10 to the culture medium storage container 20. As a result, the suspension of cells in the culture container 10 can be concentrated, whereby the amount of the liquid to be transferred to the cell collecting container 40 can be reduced. Subsequently, the thus concentrated suspension of cells is collected from the culture container 10 to the cell collecting container 40.

As mentioned above, by using the cell culture kit of this embodiment, cultivation of cells can be conducted in a closed system.

As mentioned above, according to the cell culture kit of this embodiment, in the cultivation of cells by using a culture container, a process from injection of cells, addition of a culture medium, sampling to collection can be conducted automatically while keeping a closed system in the kit. Further, since the cell culture kit of this embodiment is of the one-port configuration, only one tube pump for sending a liquid is required, whereby simplification of an apparatus can be attained.

Second Embodiment

Figure 2:
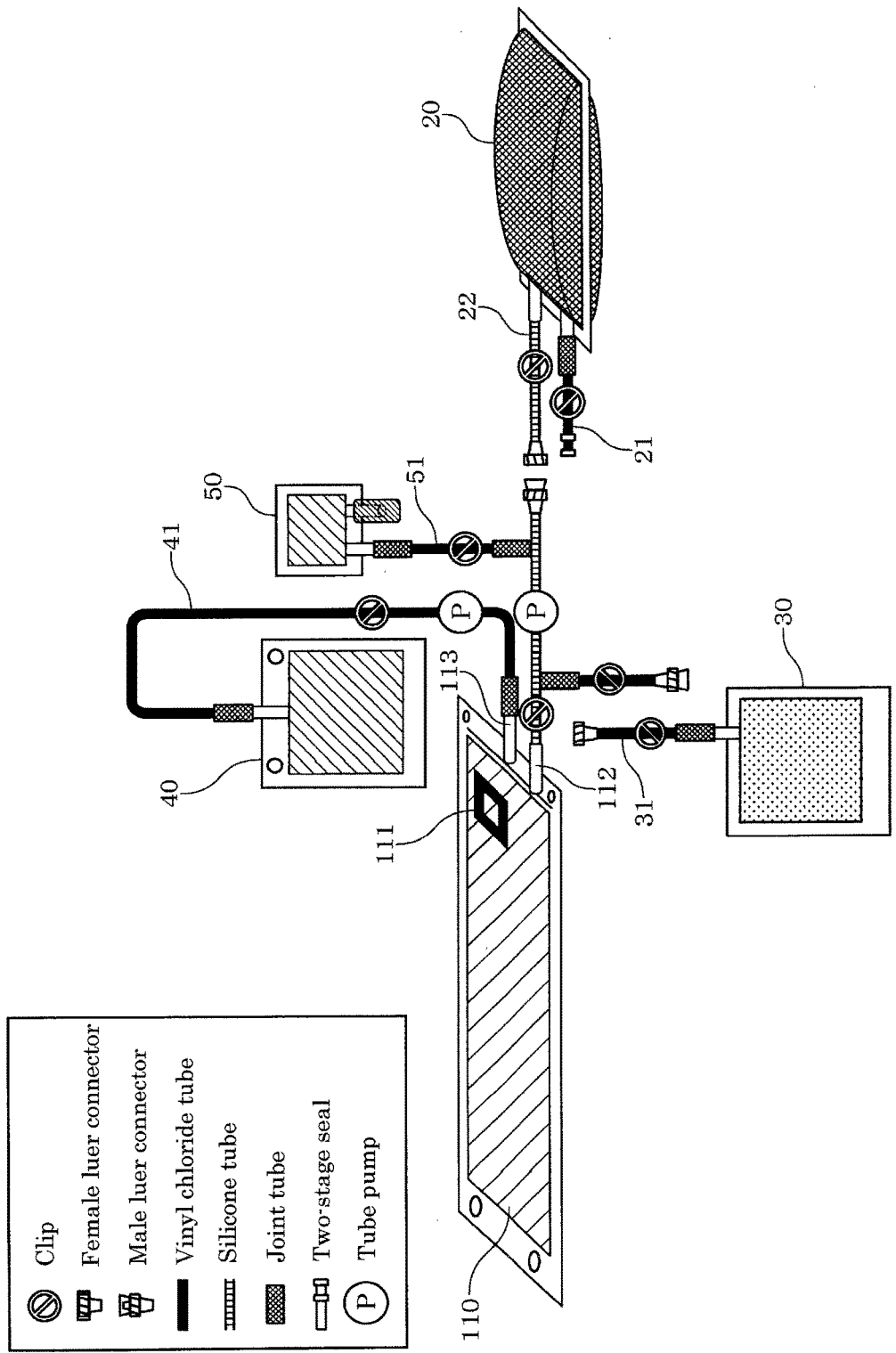
FIG. 2 is a view showing a configuration of a cell culture kit according to the second embodiment (2 port-configuration) of the present invention.

Subsequently, the second embodiment of the present invention will be explained with reference to FIG. 2. FIG. 2 is a view showing the configuration of the cell culture kit of this embodiment.

The cell culture kit of this embodiment differs from that of the first embodiment in that it is of a two-port configuration. In other points, it has the same configuration as that of the first embodiment. The cell culture kit of this embodiment be provided with a culture container 110, the culture medium storage container 20, the cell injection container 30 and the cell collecting container 40. It is preferred that the kit be provided with the sampling container 50.

As shown in FIG. 2, the culture container 110 in the cell culture kit of this embodiment is provided with a first port 112 and a second port 113.

As in the first embodiment, the first port 112 is connected to the culture medium storage container 20 is connected via the culture medium storage connecting tube 22. The second port 113 is connected to the cell collecting container 40 via the cell collecting container connecting tube 41. For each of the cell collecting container connecting tube 41 and the culture medium storage container connecting tube 22, a tube pump is used, and transfer of a culture medium and a suspension of cells are individually conducted.

Further, the cell injection container 30 is connected to the culture medium storage container connecting tube 22 via the cell injection container connecting tube 31. The sampling container 50 is connected to the culture medium storage container connecting tube 22 via the sampling container connecting tube 51.

The method for using the cell culture kit of this embodiment is the same as that of the first embodiment until cultivation of cells is completed. At the time of collecting cells, without passing through the culture medium storage container connecting tube 22, a suspension of cells can be collected in the cell collecting container 40 by means of a tube pump through the second port 113 and the cell collecting container connecting tube 41.

According to the cell culture kit of this embodiment, as mentioned above, at the time of collecting cells, without using the culture medium storage container connecting tube 22, a suspension of cells can be collected from the culture container 110 in the cell collecting container 40 by means of a dedicated tube pump. Therefore, collection of cells can be conducted more efficiently. This embodiment is one example of the two-port configuration. Instead of the cell collecting container 40, it is possible to connect the sampling container 50 via the second port 113 and the sampling container connecting tube 51.

Third Embodiment

Figure 3:
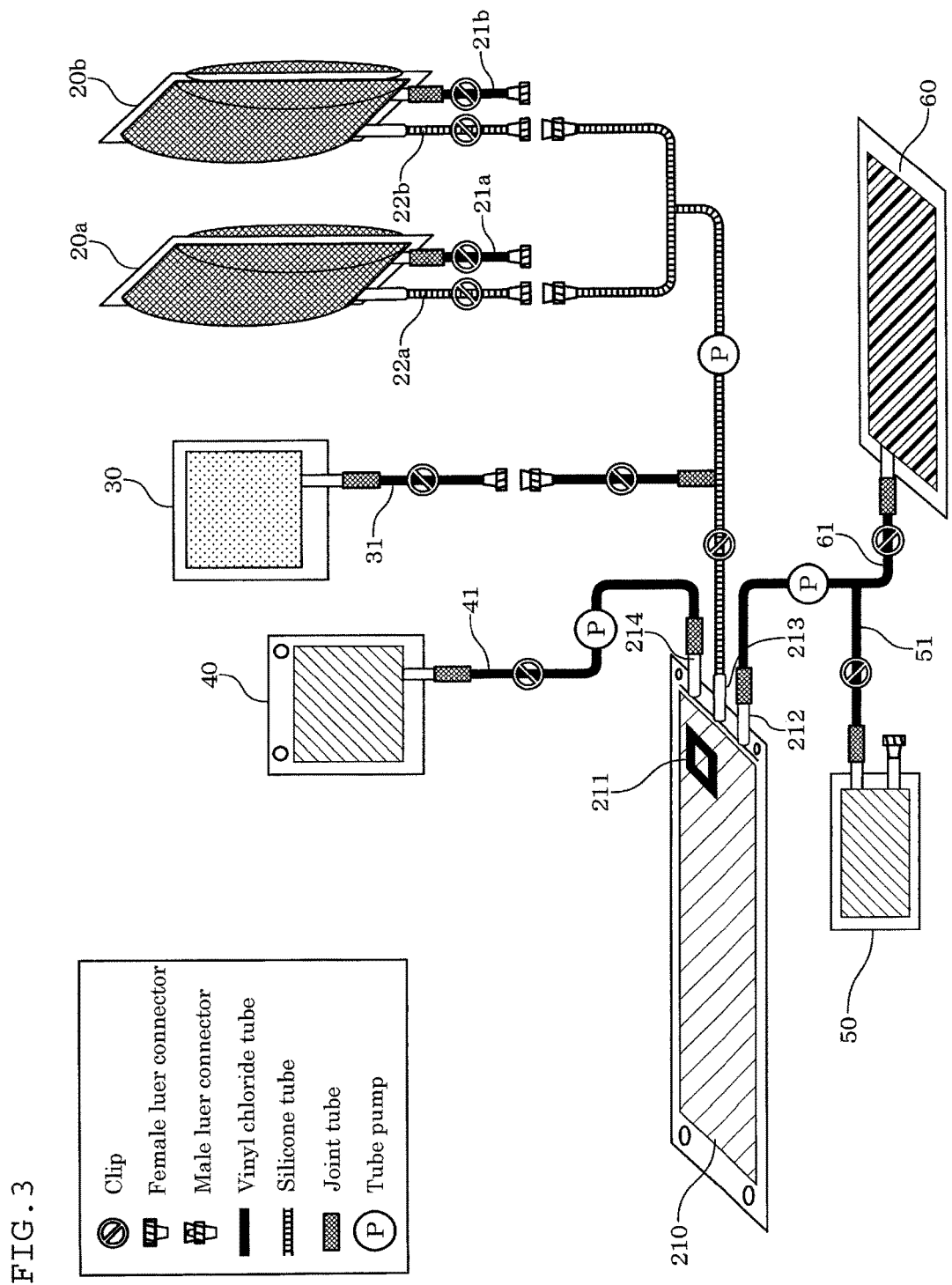
FIG. 3 is a view showing a configuration of a cell culture kit according to the third embodiment (3 port-configuration) of the present invention.

Subsequently, with reference to FIG. 3, the third embodiment of the present invention will be explained. FIG. 3 is a view showing the configuration of the cell culture kit of this embodiment.

The cell culture kit of this embodiment differs from that of the first embodiment in that it is of a three-port configuration. In other points, it has the same configuration as that of the first embodiment. That is, it is preferred that the cell culture kit of this embodiment be provided with a culture container 210, the culture medium storage container 20, the cell injection container 30, the cell collecting container 40 and a waste liquid container 60. The sampling container 50 is also preferably provided. Further, as the culture medium storage container 20, two containers, i.e. culture medium storage containers 20a and 20b, are provided.

As shown in FIG. 3, the culture container 210 in the cell culture kit of this embodiment is provided with a first port 212, a second port 213 and a third port 214.

In this embodiment, this first port is connected to the sampling container 50 and the waste liquid container 60, respectively, via the sampling container connecting tube 51 and the waste liquid container connecting tube 61. Further, in a tube portion where these tubes are joined, a tube pump is used, and transfer of a suspension of cells to the sampling container 50 and transfer of a supernatant to the waste liquid container 60 are respectively conducted.

The second port 213 is connected to the culture medium storage containers 20a and 20b via the culture medium storage container connecting tubes 22 (22a and 22b). By using a plurality of culture storage containers in this way, it is possible to transfer a combination of culture mediums having different compositions to the culture container 10. Further, it is also possible to vary the composition of a culture medium to be supplied and the timing of the supply or the like. A tube pump is used in the culture medium container connecting tube 22, transfer of a culture medium to the culture container 210 is conducted.

The third port 214 is connected to the cell collecting container 40 via the culture medium collection container connecting tube 41, the cell collecting container 40. By means of the tube pump, a suspension of cells is transferred from the culture container 210 to the cell collecting container 40.

The method for using the cell culture kit of this embodiment is the same as that of the first embodiment until cultivation of cells starts. For the sake of a restricted space in the drawing, in FIG. 3, the cell injection container connecting tube 31 is connected to the middle of the culture medium storage container connecting tube 22. Actually, in order to prevent entering of air in the culture container 210, it is preferable to connect to a position close to the second port.

During cultivation of cells, by appropriately transferring a sample from the culture container 210 to the sampling container 50, the sample can be used for examination or analysis.

Further, after completion of cultivation of cells, a supernatant of a suspension of cells is transferred from the culture container 210 to the waste liquid container 60 via a waste liquid container connecting tube 61, whereby the suspension of cells in the culture container 210 can be concentrated. Finally, the thus concentrated suspension of cells is collected from the culture container 210 to the cell collecting container 40.

According to the cell culture kit of this embodiment, a plurality of operations can be conducted simultaneously. In particular, even if a culture medium remains in the culture medium storage container 20 or the culture medium storage container connecting tube 22, it is possible to conduct sampling in the sampling container 50, and timing of supply of a culture medium and sampling can be adjusted flexibly.

Fourth Embodiment

Figure 4:
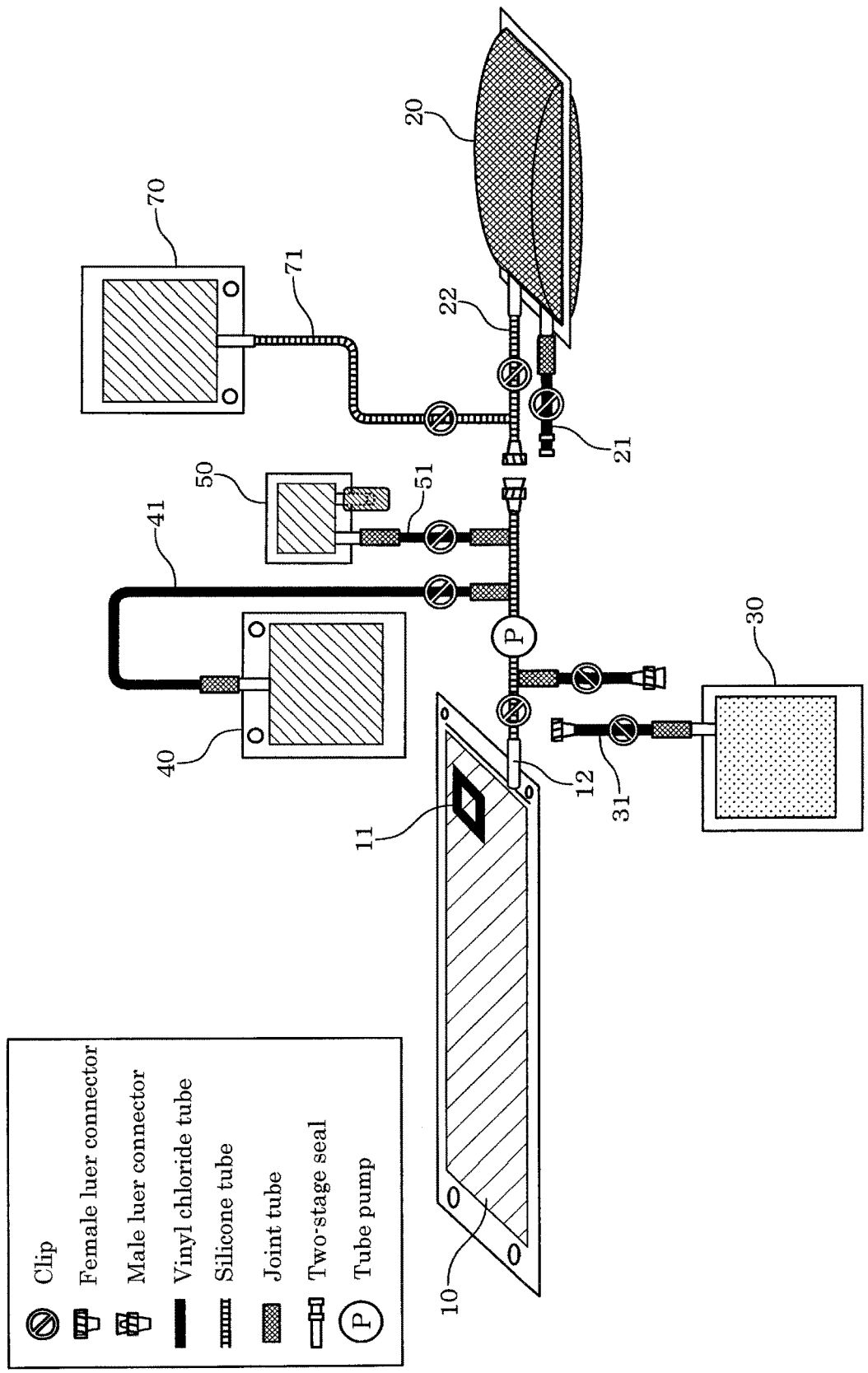
FIG. 4 is a view showing a configuration of a cell culture kit according to the fourth embodiment (1 port-configuration) of the present invention.
Figure 5:
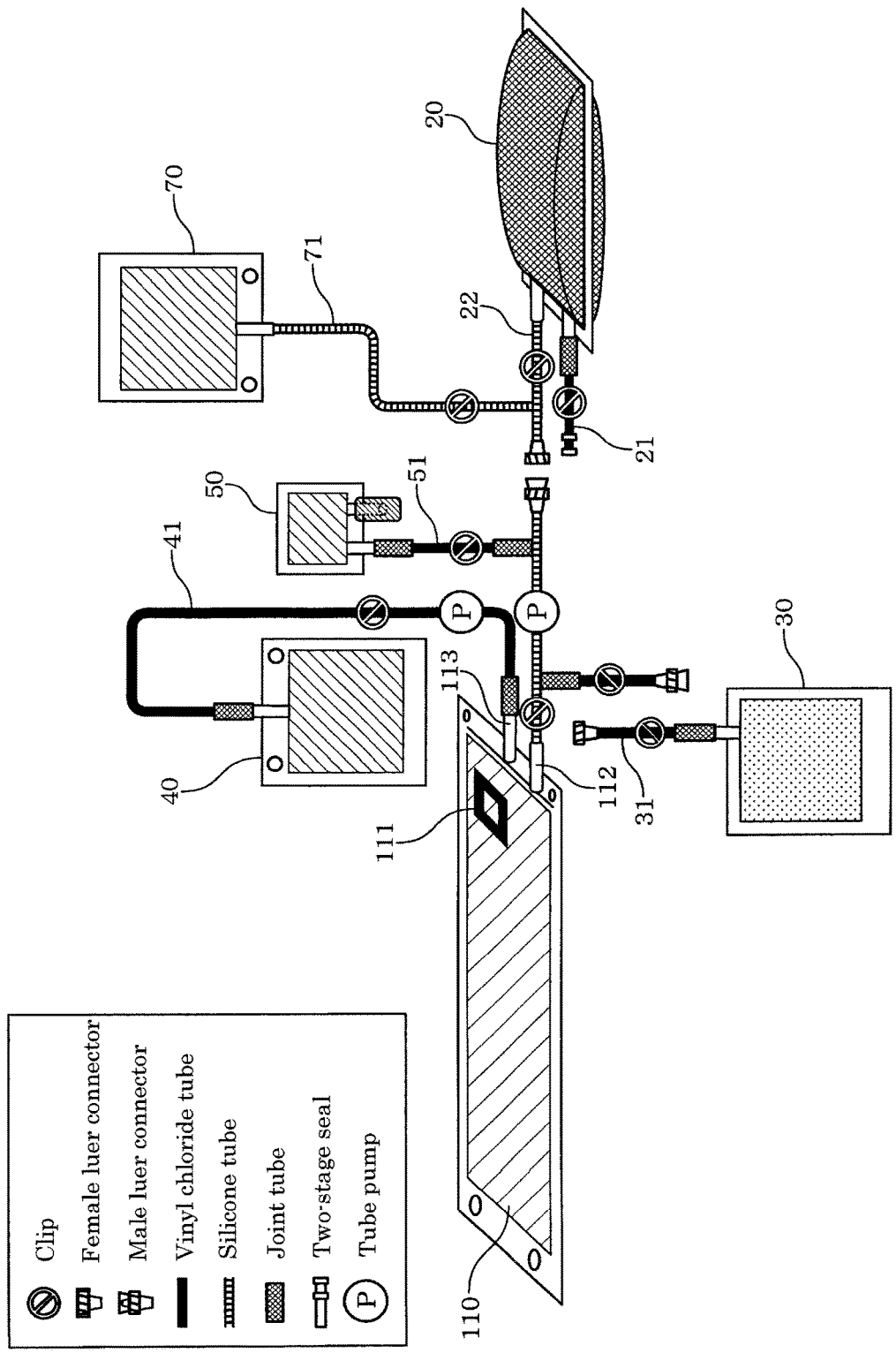
FIG. 5 is a view showing a configuration of a cell culture kit according to the fourth embodiment (2 port-configuration) of the present invention.
Figure 6:
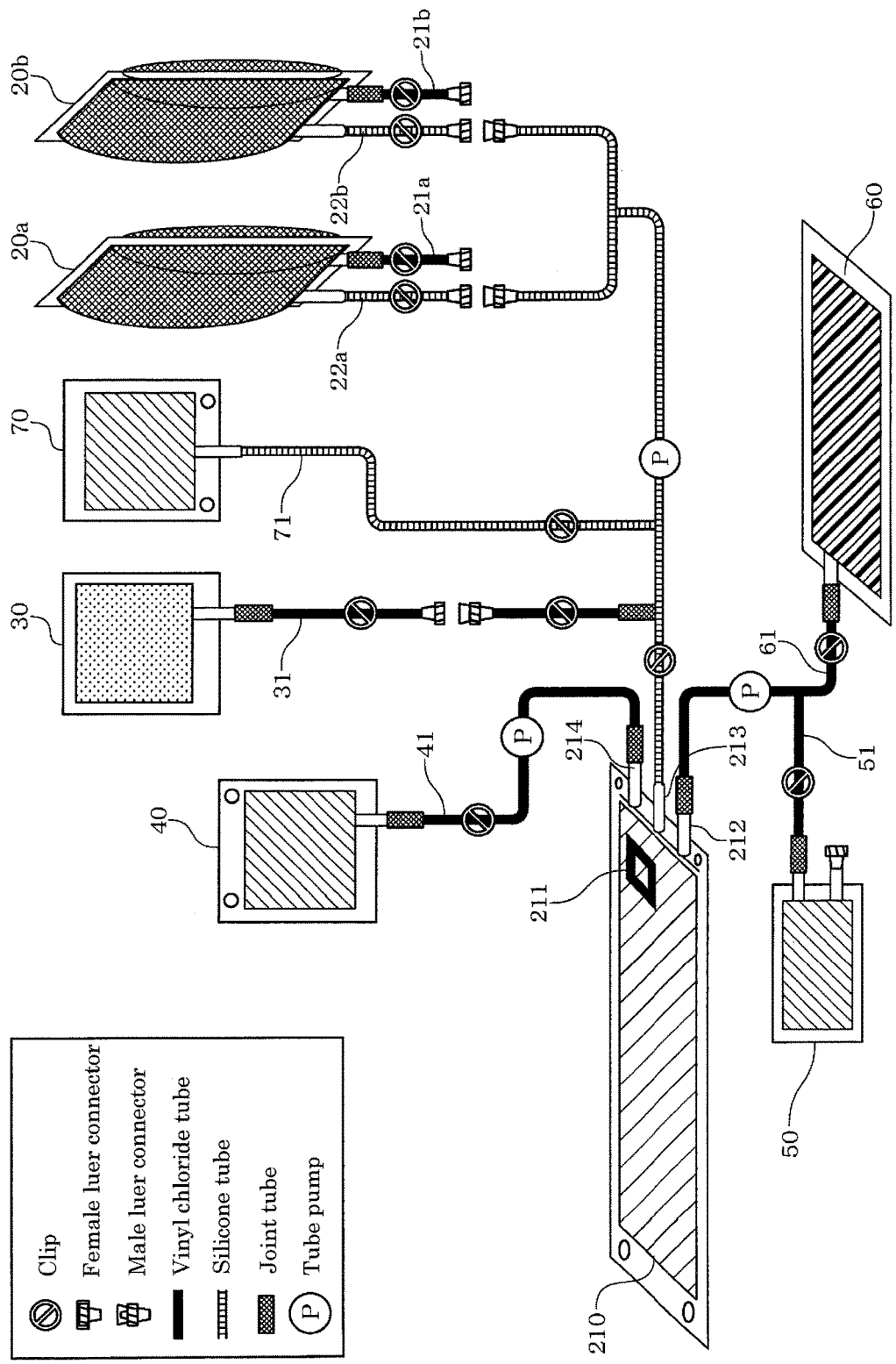
FIG. 6 is a view showing a configuration of a cell culture kit according to the fourth embodiment (3 port-configuration) of the present invention.

Next, with reference to FIGS. 4 to 6, the fourth embodiment of the present invention will be explained. These figures are views showing the configuration of the cell culture kit of this embodiment.

The cell culture kit of this embodiment is characterized in that, in addition to the configurations of the first to third embodiments, it is provided with a temperature control container 70 for controlling the temperature of a culture medium and a temperature control container connecting tube 71. Other configurations are the same as those in the first to third embodiments.

Hereinbelow, an explanation will be made with reference to FIG. 4 on the cell culture kit of this embodiment in which, to the cell culture kit of the first embodiment, the temperature control container 70 and a temperature control container connecting tube 71 are added. The same can be applied to the temperature control container 70 and the temperature control container connecting tube 71 in FIGS. 5 and 6.

The temperature control container 70 is a container for controlling the temperature of a culture medium by temporarily storing a culture medium to be transferred when transferring a culture medium from the culture medium storage container 20 to the culture container 10. No specific restrictions are imposed on the amount of a culture medium to be transferred, and it may be part or all of a culture medium in the culture medium storage container 20. When a plurality of culture medium storage containers 20 are provided in the cell culture kit and part of these culture medium storage containers 20 store various substances other than a culture medium, e.g. a physiologically active substance or cytokine, that are to be added to a culture medium in the culture medium 10 during cultivation, it is possible to heat these substances by the temperature control container 70. It is preferred that the container for the temperature control container 70 have gas barrier properties as in the case of the culture medium storage container 20.

At least one port is provided in the temperature control container 70. The temperature control container connecting tube 71 is connected to the port. The temperature control container connecting tube 71 is connected to the culture medium storage container connecting tube 22 that connects the culture medium storage container 20 and the culture container 10. That is, the temperature control container 70 is branched from the tube that connects the culture medium storage container 20 and the culture container 10, and is provided in the cell culture kit while keeping a closed system. The temperature control container connecting tube 71 and the culture medium storage container connecting tube 22 may be integrally formed.

The temperature control container 70 is preferably formed of a soft package material. It is also preferred that it have a configuration in which a ventilation is provided. If a culture medium is heated in the temperature control container 70, a gas that has been dissolved in the culture medium is escaped. At this time, by allowing the port of the temperature control container 70 to be directed downward, the gas can be collected in the upper part of the temperature control container 70, whereby only a culture medium can be sent to the culture container 10. As a result, it becomes possible to transfer a culture medium without mixing in of excessive air bubbles in the culture container 10.

It is preferred that the temperature control container 70 be arranged inside the incubator where the culture container 10 is provided. In this case, it becomes possible to adjust the temperature of a culture medium inside the temperature control container 70 be the same temperature as that inside the culture container 10. As for the temperature, it can be 37° C., for example.

Further, it is preferred that the temperature control container 70 be provided outside the incubator such that the temperature control container 70 be heated by a separate heating device to adjust the temperature of a culture medium inside the temperature control container 70. In this case, the temperature can be controlled to a range of 30 to 37° C., for example.

In addition, by arranging the temperature control container 70 outside the incubator, and allowing it to stand without providing the heating device, it is possible to return the temperature of a culture medium inside the temperature control container 70 to normal temperature (room temperature).

In the cell culture kit of this embodiment, two or more temperature control containers 70 be provided. Due to such a configuration, it becomes possible to control the temperature of the twice or more the amount of a culture medium or other materials simultaneously.

As for the temperature control container connecting tube 71, since it is used for transferring a culture medium to the culture container 10 little by little throughout the cultivation period, it is desirable to have especially excellent low cytotoxicity, low elution properties or the like, and it is not required to fuse it during the process of cultivation. Therefore, the temperature control container connecting tube 71 is preferably the same as that of the culture medium storage container connecting tube 22 that connects the culture container 10 and the culture medium storage container 20.

As mentioned above, according to the cell culture kit of this embodiment, after heating a culture medium in a temperature control container in an amount required for transferring to a culture container, a culture medium can be then transferred to the culture container.

As a result, the temperature of a culture medium in the culture container is not lowered, whereby hindering of proliferation of cells can be prevented.

Since a culture medium can be heated by a temperature control container, a culture medium in a culture medium storage container can be stored in a refrigerator. As a result, if the heating time of a culture medium is prolonged, occurrence of a problem that the proliferation efficiency of cells is lowered can be prevented.

In addition, since gas that has been dissolved in a culture medium is escaped by heating, only a culture medium can be transferred from the temperature control container to the culture container, whereby mixing in of air bubbles in the culture container can be prevented.

The present invention is not restricted by the above-mentioned embodiments, and it is needless to say various modifications can be possible within the scope of the present invention.

For example, in the embodiments, an example in which a tube of a specific size is used is given, and a specific connector is used. In the scope of technology of the present invention, appropriate modifications are possible. For example, other elements that attain the same functions can be used. Further, a container filled with various substances such as a physiologically active substance or cytokine that is to be added to a culture medium during cultivation can be additionally attached to the kit of the embodiments.

INDUSTRIAL APPLICABILITY

The present invention can be preferably used in the fields of biomedicines, regenerative therapy, immune therapy or the like where a large amount of cells is required to be cultivated.

The invention claimed is:

1. A cell culture kit for cultivating cells in a closed system, comprising:
    a culture container for cultivating cells;
    a culture medium storage container for storing a culture medium;
    a cell injection container; and
    a cell collecting container for collecting a suspension of cells after cultivation, wherein
    the culture medium storage container collects the culture medium after cultivation,
    the culture container, the culture medium storage container, the cell injection container, and the cell collecting container are linked to one another through a conduit,
    the cell injection container is a bag that is branched from a first position in the conduit linking the culture medium storage container and the culture container, wherein the first position is located immediately proximate to the culture container,
    the culture medium stored in the culture medium storage container is transferred into the cell injection container, in which the cells required at the time of starting cultivation are included, with air in the conduit through the conduit at the first position, and
    the cells are injected together with the culture medium from the cell injection container into the culture container at the first position.

2. The cell culture kit according to claim 1, further comprising at least one or more of a sampling container sampling part of a suspension of cells being cultured, wherein the sampling container is linked to the culture container through the conduit.

3. The cell culture kit according to claim 1, further comprising at least one or more of a waste liquid container for collecting the culture medium during or after cultivation, wherein the waste liquid container is linked to the culture container through the conduit.

4. The cell culture kit according to claim 1, further comprising an additional culture medium storage container, wherein the same culture medium or different culture media are filled in each of the culture medium storage container.

5. The cell culture kit according to claim 1, further comprising a temperature control container for controlling the temperature of the culture medium, wherein the temperature control container is branched from the conduit linking the culture container and the culture medium storage container.

6. The cell culture kit according to claim 5, wherein the culture medium is refrigerated in the culture medium storage container, and a part or all of the culture medium is transferred to the temperature control container and is heated to a predetermined temperature, and then transferred to the culture container.

7. The cell culture kit according to claim 1, wherein each of the containers is made of a flexible material in the form of a bag.

8. The cell culture kit according to claim 1, wherein the culture medium storage container has a carbon dioxide transmittance of 1000 ml/m$^2$·day·atm (23° C.-80% RH) or less and the culture container has an oxygen transmittance of 5000 ml/m$^2$·day·atm (37° C.-80% RH) or more.

9. The cell culture kit according to claim 1, wherein the culture medium storage container has at least two conduits, and a conduit that is not linked to the culture container is formed of a soft vinyl chloride resin.

10. The cell culture kit according to claim 2, wherein at least a part of the conduit is formed of a thermoplastic resin, and the part of the conduit is connected to the cell injection container, the cell collecting container, or the sampling container.

11. The cell culture kit according to claim 1, wherein at least one of the culture medium storage container and the cell injection container can be removed from the cell culture kit.

12. The cell culture kit according to claim 1, wherein a part of the conduit linking the culture medium storage container and the culture container is made of polyolefin or a silicone resin.

13. The cell culture kit according to claim 1, wherein the culture container, the culture medium storage container, the cell injection container, and the cell collecting container form a closed system.

14. The cell culture kit according to claim 1, wherein the cell collecting container is branched from a second position in the conduit, and wherein the second position is located between the first position and the culture medium storage container.

15. A method for using the cell culture kit according to claim 1, comprising:
    transferring the culture medium from the culture medium storage container to the cell injection container while moving air inside the conduit connecting the culture medium storage container and the cell injection container to the cell injection container,
    injecting the cells together with the culture medium from the cell injection container to the culture container, and transferring the culture medium from the culture medium storage container to the culture container.

\* \* \* \* \*